United States Patent [19]

Foti

[11] 4,190,033
[45] Feb. 26, 1980

[54] CLOSED FLOW CALORIC TEST METHOD

[76] Inventor: Thomas M. Foti, 10937 Deborah Dr., Potomac, Md. 20854

[21] Appl. No.: 926,718

[22] Filed: Jul. 21, 1978

Related U.S. Application Data

[63] Continuation of Ser. No. 771,340, Feb. 23, 1977, abandoned, which is a continuation-in-part of Ser. No. 734,291, Oct. 21, 1976, abandoned.

[51] Int. Cl.² ............................................. A61B 5/00
[52] U.S. Cl. .................................. 128/742; 128/401; 128/151; 128/746
[58] Field of Search ....... 128/2 Z, 2 R, 2 N, 399–401, 128/151, 152, 303.11, 303.12, 742, 746

[56] References Cited

U.S. PATENT DOCUMENTS

| | | | |
|---|---|---|---|
| 550,238 | 11/1895 | Allen, Jr. | 128/401 |
| 1,652,954 | 12/1927 | Pierce | 128/401 |
| 3,000,271 | 9/1961 | Harvey et al. | 128/2.1 M |
| 3,125,096 | 3/1964 | Antiles et al. | 128/401 |
| 3,227,154 | 1/1966 | Cook | 128/401 X |
| 3,460,538 | 8/1969 | Armstrong | 128/401 X |
| 3,467,104 | 9/1969 | Burbridge et al. | 128/401 X |
| 3,496,942 | 2/1970 | Shipley | 128/401 |
| 3,736,929 | 6/1973 | Mills | 128/152 |

FOREIGN PATENT DOCUMENTS 187217  3/1967  U.S.S.R. ................... 128/2 N

OTHER PUBLICATIONS

Ono, H. et al., Revuedelaryngologie, Otologie, Rhinologie, May–Jun., 1976, pp. 223–230.
Vestnik Otorinolaringologii, No. 2, 1962, pp. 93, 94.

*Primary Examiner*—Kyle L. Howell
*Attorney, Agent, or Firm*—Bacon & Thomas

[57] ABSTRACT

A method of caloric vestibular testing comprises inserting an inflatable receptacle into an ear canal; admitting pressurized calorized fluid into the receptacle to cause its expansion laterally within the ear canal and longitudinally up to the tympanic membrane, such expansion filling the cross-sectional area of at least a portion of the ear canal; while inflating the receptacle, venting air trapped between the receptacle and the tympanic membrane to atmosphere; and circulating a volume of calorized liquid through the receptacle while carrying out a caloric vestibular function testing procedure.

4 Claims, 10 Drawing Figures

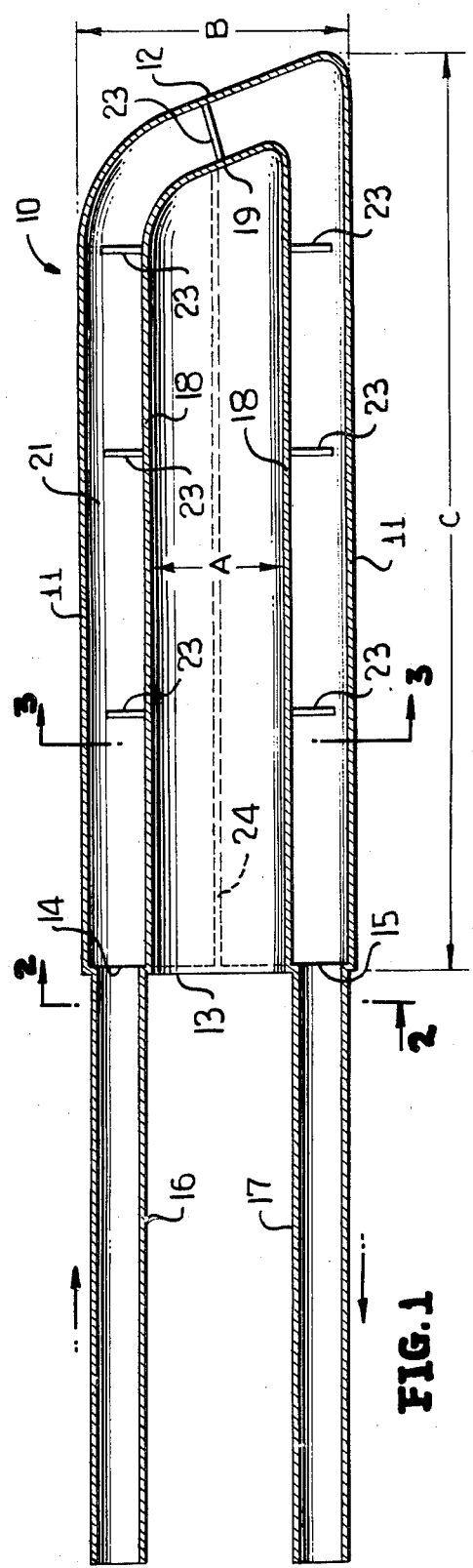
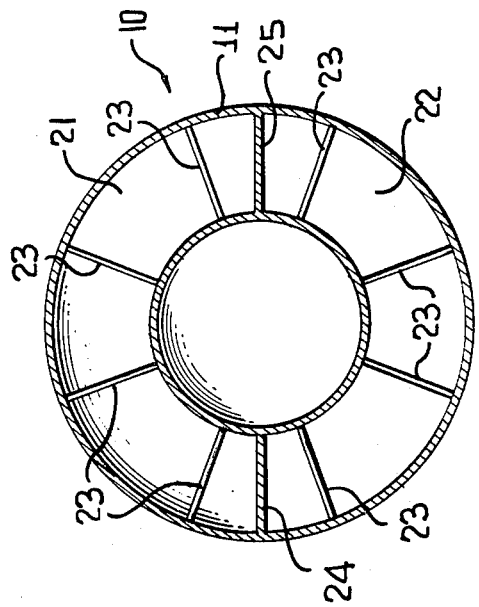
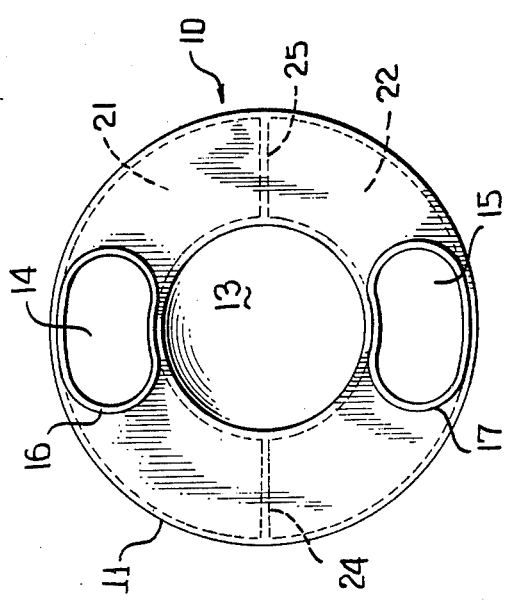

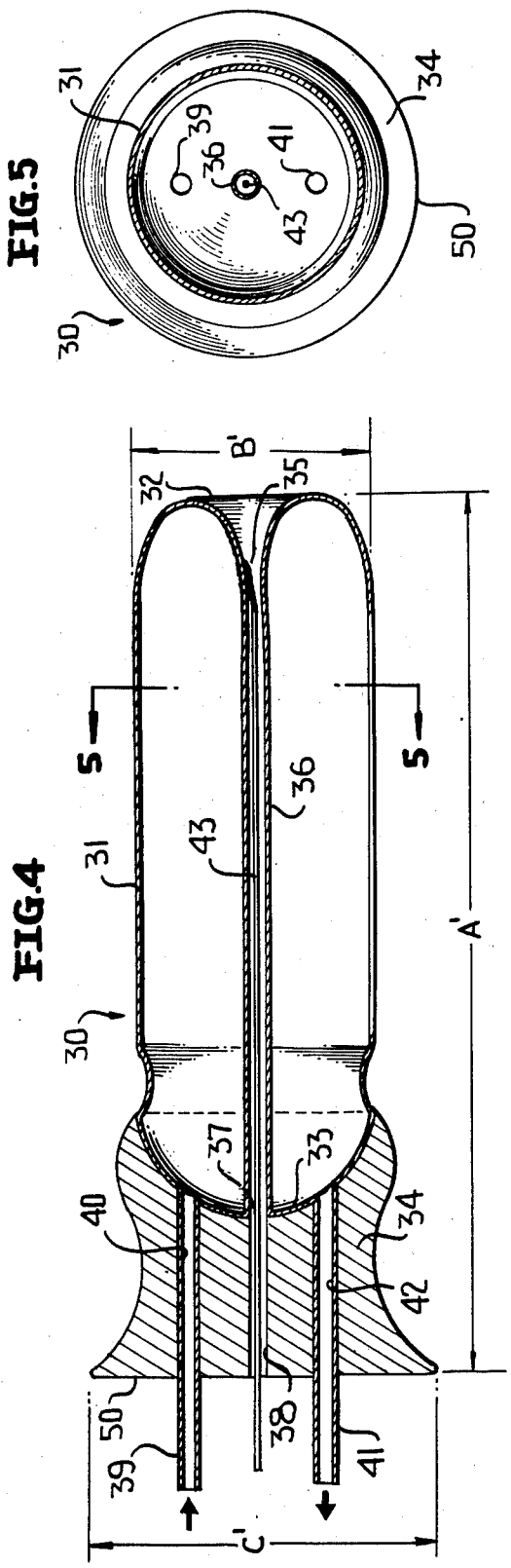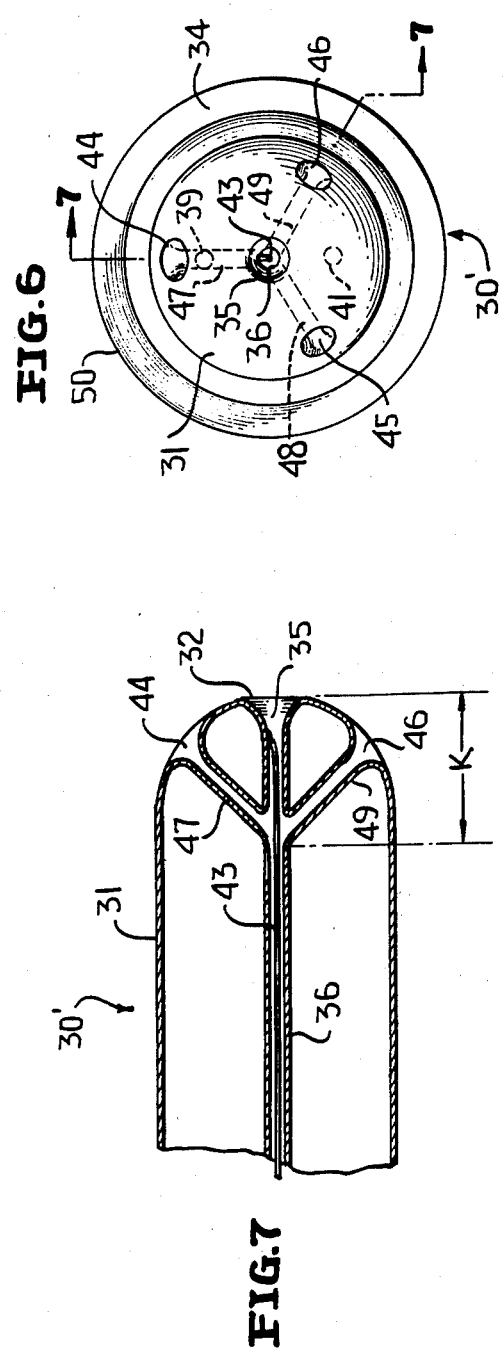

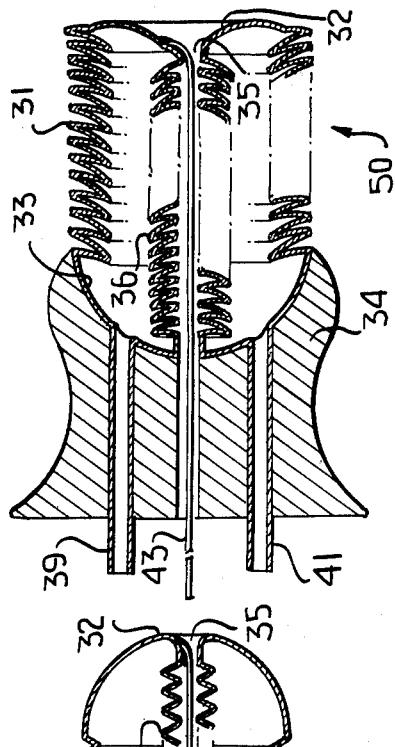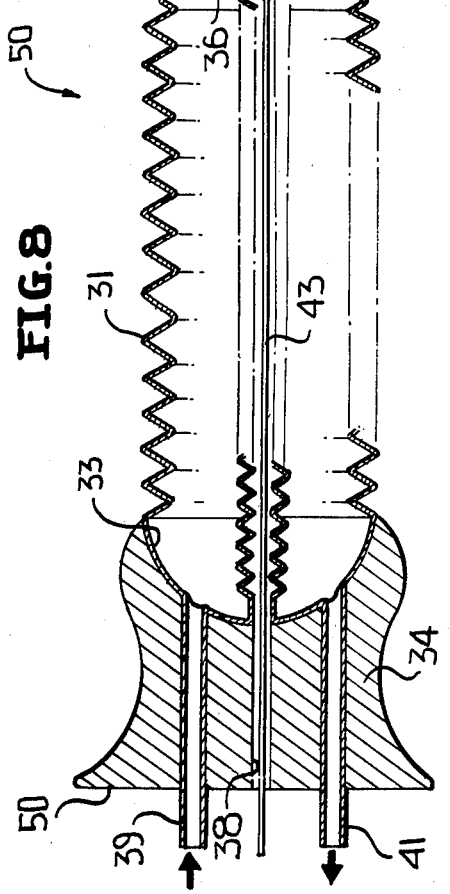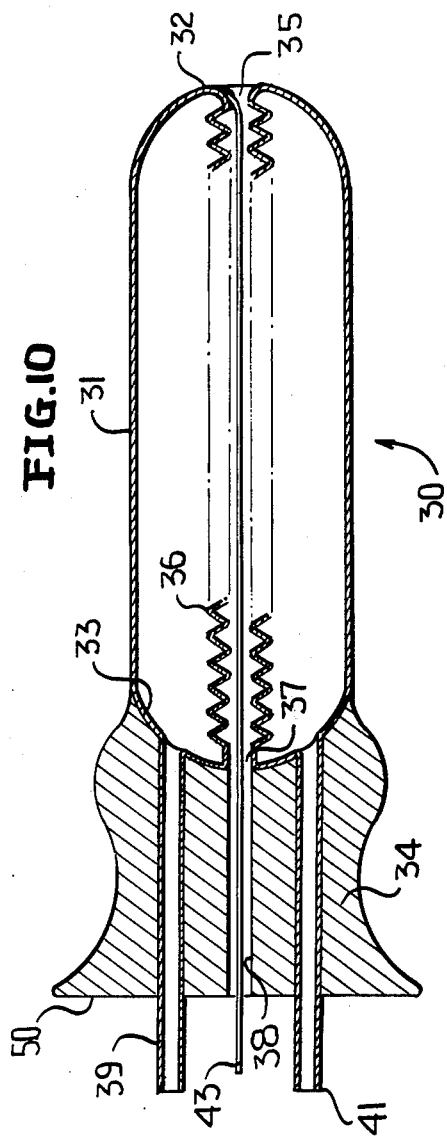

CLOSED FLOW CALORIC TEST METHOD

This application is a continuation of application Ser. No. 771,340, filed Feb. 23, 1977, now abandoned, which was a continuation-in-part of application Ser. No. 734,291, filed Oct. 21, 1976, now abandoned.

BACKGROUND OF THE INVENTION

The present invention relates to a method for caloric or nystagmus testing. More particularly, the present invention relates to improvements which simplify the inducing of nystagmus and greatly expand the practical utility of caloric nystagmus testing.

Nystagmus is a regular, alternating eye movement of variable velocity which can be induced by many known methods. It is well-recognized that by monitoring controllably-induced nystagmus a diagnostician can ascertain various vestibular disorders as well as other isolated clinical pathology as may pertain to various medico-surgical subspecialties. Measurement of nystagmus can be done visually or by electronic apparatus, either of which may be employed in conjunction with the present invention.

Caloric nystagmus testing involves the injection of specified fluid volumes at known temperatures into the patient's ear to induce a nystagmus response. The most widely used fluid for caloric testing is water. However, water necessarily overflows the patient's ear, is uncomfortable for the patient, is messy to handle, and requires much maintenance. Further large amounts of water are required, all of which must be heated from ambient temperature to specific temperatures above ambient. Air has also been used as a caloric test fluid but often causes undue patient discomfort; furthermore, variability of test results have been observed due in part to the lower heat capacity of air and sensitivity to applicator positioning. Open (i.e. overflowing) water caloric testing is medically contraindicated for patients having: a hole in the ear drum; an ear infection; a prior surgically-created cavity in the ear; or middle ear ventilating tubes.

It is an object of the present invention to provide a method for conducting caloric tests without the aforementioned disadvantages.

It is another object of the present invention to provide a method for conducting caloric tests without requiring injection of fluid directly into the ear.

It is still another object of the present invention to provide a method of conducting caloric nystagmus tests without flowing air or water directly into the patient's ear.

It is still another object of the present invention to provide an energy-conserving technique for inducing nystagmus, saving on both water and heating consumption.

There has been some suggestion in the prior art that caloric testing can be performed by the finger-cot method whereby a balloon-like member is inserted in the ear and the test liquid is caused to flow into that member. In practice, however, it has been found that introduction of the balloon-like member into the ear is extremely difficult; moreover, the measurement has proven highly insensitive and many of the disadvantages of direct flow into the ear (mess, undue pressure build-up, etc.) remain. Further, there is a danger that the finger-cot, when expanded, will be too deep within the ear canal, resulting in damage to the tympanic membrane from pressure build-up.

It is a further object of the present invention to provide a method for performing caloric nystagmus tests without the need for directly flowing test fluid into the ear and without the disadvantages of the finger-cot approach.

SUMMARY OF THE INVENTION

In accordance with the present invention a probe or receptacle, which provides an internal flow path for caloric test fluid, is provided. The probe is made of extremely thin, durable and flexible material capable of efficiently transferring thermal energy from test fluid in the probe to the patient's ear canal and tympanic membrane. In one embodiment the probe is semi-rigid, to facilitate insertion into the ear canal, and is of predetermined length to assure that it does not rupture the tympanic membrane when expanded under the pressure of test fluid to conform to the canal. If desired, the forward end of the probe may be contoured to match the tympanic membrane. It is also possible to provide flow-directing vanes internally of the probe to establish a desired flow path for test fluid.

In other embodiments an ear mold is provided and contoured to match the tragus region of the ear, which region is a key anatomical landmark for depth insertion into the ear canal. The ear mold may be considered a stop member and has a distensible, inflatable balloon-like member attached to its forward end, the balloon-like member preferably being deflated during insertion of the probe. The ear mold establishes a standard insertion depth and has inflow and outflow passages for test fluid defined therethrough. The balloon-like member serves as a receptacle for test fluid and when inflated by the test fluid it expands to the contour of the ear canal and effects nystagmus inducing thermal transfer. An air vent passage is provided through the balloon and ear mold to permit evacuation of air trapped in the ear between the expanding balloon and the ear drum; the hermetically-sealing ear mold renders this vent passage particularly important. The balloon member, as well as the vent passage, can be corrugated at least in part, and a depth indicator can be provided. The inlet to the vent is inwardly conically shaped to prevent injury or irritation to the tympanic membrane, and plural inlets can be provided.

BRIEF DESCRIPTION OF THE DRAWINGS

The above and still further objects, features and advantages of the present invention will become apparent upon consideration of the following detailed description of one specific embodiment thereof, especially when taken in conjunction with the accompanying drawings, wherein:

FIG. 1 is a side view in section of one embodiment of the probe of the present invention;

FIG. 2 is a view in section taken along lines 2—2 of FIG. 1;

FIG. 3 is a view in section taken along lines 3—3 of FIG. 1;

FIG. 4 is a side view in section of another embodiment of the present invention;

FIG. 5 is a view in section taken along lines 5—5 of FIG. 4;

FIG. 6 is an end view in plan of still another embodiment of the present invention;

FIG. 7 is a view in section taken along lines 7—7 of FIG. 6;

FIG. 8 is a side view in section of still another embodiment of the present invention shown in partially expanded state;

FIG. 9 is a side view in section of the embodiment of FIG. 8 shown in partially collapsed state; and FIG. 10 is a side view in section of still another embodiment of the present invention.

DESCRIPTION OF PREFERRED EMBODIMENTS

Referring specifically to the drawings, a generally cylindrical probe or receptacle assembly 10 comprising one form of the present invention is proportioned to permit insertion of its distal end area (to the right as illustrated) into a patient's ear along the longitudinal dimension of the probe. The probe has a semi-rigid, hollow portion defined by outer wall 11, of generally cylindrical configuration, which is contoured at its distal end surface 12 to generally match the contour of the tympanic membrane of the human ear. More specifically, the distal end surface 12 is sloped so that its bottom portion projects beyond its top portion, as illustrated. The outer wall 11 is shown in its inflated, distended position in FIG. 1, but normally would be somewhat smaller in its relaxed state.

The opposite or proximal end 13 of the probe is generally circular and has a test fluid inlet opening 14 and a test fluid outlet opening 15 defined therein. Inlet opening 14 is defined in the top semi-circle of end surface 13 and communicates with an inlet flow tube 16. Outlet opening 15 is disposed in the bottom semi-circle of end surface 13 and communicates with an outlet flow tube 17.

A generally coaxial interior wall 18 of the probe is also of generally cylindrical configuration and is substantially equidistant from outer wall 11 at all points along its length. In addition, wall 18 has an end portion 19 which is similarly spaced from end surface 12 of the outer wall 11.

The annular space between walls 11 and 18 is divided into upper and lower halves 21 and 22, respectively, by flat, longitudinally-extending horizontal vanes 24 and 25 that serve to guide incoming test fluid to the distal end of receptacle 10. Upper half 21 communicates with inlet tube 16 via inlet opening 14 and comprises a fluid inflow path within the probe 10. Lower half 22 communicates with outflow tube 17 via outlet opening 15 and comprises a fluid outflow path within the probe 10. A plurality of struts 23 are secured between walls 11 and 18 at various locations.

In performing a caloric nystagmus test with probe 10, calorized inlet fluid at the desired temperature is caused to flow into the probe via inlet tube 16. The fluid is preferably a liquid, because it has greater heat transfer characteristics than a gas, and may be water. The inflowing liquid flows in through the upper half 21 of probe 10, between the ends 12 and 19 of walls 11 and 18, respectively, and out through the lower half 22 of the probe and outlet tube 17. When the probe is properly inserted in a patient's ear and inflated with end surface 12 against the patient's tympanic membrane, efficient thermal transfer between the flowing fluid and the tympanic membrane takes place through outer wall 11. This thermal transfer induces the nystagmus response which can be monitored by any available apparatus or technique.

The pressure of the flowing fluid tends to expand outer wall 11 to more readily match the contour of the external auditory canal and tympanic membrane, thereby providing for more efficient thermal transfer between the fluid and the ear. The pressure of the fluid also tends to separate the walls 11 and 18, which separation is restrained by struts 23.

It is important that the material employed in the probe be extremely thin to permit efficient thermal transfer between the fluid and the tympanic membrane and ear canal. In addition the material must be durable, to prevent rupture, and flexible, to permit optimum conformance to the ear surface when the pressurized test liquid is flowing through the probe. Moreover, the material must be semi-rigid; that is, it must have sufficient rigidity to permit easy insertion of the probe into the patient's ear. Certain types of polyurethane or silicone rubber are well suited to provide these characteristics. By way of example only, a segmented polyether polyurethane product sold by Ethicon, Inc., of Somerville, New Jersey, under the trademark BIOMER, is suitable for use in probe 10, particularly in the thicknesses of approximately 0.125 mm. Likewise, a silicone elastomer suitable for use at a thickness of approximately 0.125 mm. (or special thinner formulations) is marketed by Dow Corning Corporation of Midland, Michigan, under the trademark SILASTIC. Various other materials are suitable as will be appreciated by those skilled in this field.

The tubes 16 and 17 can be made of any flexible material which readily bonds to the probe material and which is not adversely affected by the test liquid. The tubes may be color-coded, if desired, or otherwise marked to distinguish the upper or inlet tube 16 from the lower or outlet tube 17. This assures proper orientation of the probe so that surface 12 abuts the tympanic membrane.

The dimensions of the probe depend upon whether it is intended for use in an average-sized adult's ear or a child's ear. By example only, typical dimensions for adult use are as follows:

| | |
|---|---|
| A (inner diameter of cylindrical wall 18) | 3 mm |
| B (outer diameter of probe) | 6 mm |
| C (length of probe) | 32 mm |
| Thickness of walls 11, 18 | 0.025 to 0.25 mm |
| Length of tubes 16, 17 | approximately 30 mm (as needed) |

Another embodiment of the present invention is probe or receptacle assembly 30 illustrated in FIGS. 4 and 5. Probe assembly 30 includes an elongated balloon-like member 31 having a distal area termination in closed end 32 and a proximal end 33 at the proximal area of the assembly 30. Member 31 is preferably fabricated from the same type of plastic material described above for probe 10; however, because of the absence of internal struts 23 or equivalent, member 31 is collapsible when not inflated by test fluid. The proximal end 33 of member 31, in this embodiment is secured (by means of adhesive material, thermal or chemical bonding, etc.) to the distal concave end of an ear mold 34. Alternatively, balloon-like member 31 and ear mold 34 may be formed as part of the same molded piece. The ear mold 34 preferably has some flexibility but in any case has sufficient rigidity to be inserted into and hermetically seal a patient's ear. For this purpose the ear mold 34 is contoured to match the walls of the outer portion of the cartilagenous auditory canal. (It will be appreciated that different size ear molds may be used for children and adults.) The ear mold widens at its proximal end 50 to limit the extent to which member 31 and the distal end of the ear mold can enter an ear canal.

When fully expanded, member 31 is of generally cylindrical configuration with ends 32 and 33 rounded. A generally conical or funnel-shaped inwardly convergent recess 35 is defined in member 31 centrally of forward end 32 where duct 36 and member 31 meet with each other. Recess 35 communicates at its narrow end with a flexible air tube 36 extending longitudinally from recess 35 through member 31 to a hole 37 defined in end 33, the tube 36 defining a separate fluid flowpath from the test fluid inlet and outlet. Tube 36 may be accordian-pleated or corrugated as described in relation to FIGS. 8, 9 and 10, below; importantly, tube 30 must have sufficient radial strength to prevent it from collapsing when member 31 is pressurized with test liquid. The air tube 36 is confined within the external boundaries of balloon 31 to prevent any projections from contacting the tympanic membrane. The conical inlet or recess 35 likewise prevents irritation to the membrane and prevents the inlet from sealing up while the balloon is expanding within the ear canal and towards the tympanic membrane. A bore 38, extending longitudinally through ear mold 34, communicates with air tube 36 at hole 37. A fluid inlet tube 39 extends through another bore 40 defined through ear mold 34 to provide a flow path for test fluid into balloon-like member 31 from beyond the proximal end 50 of the ear mold. A fluid outlet tube 41 extends through still another bore 42 defined through ear mold 34 to provide a flow path for test fluid out of balloon-like member 31 to beyond the proximal end 50 of the ear mold.

It should be noted that the test fluid inlet and outlet tubes need not be integral parts of the balloon-like member 31 as shown; rather, they may be separate tubes which can be inserted part way into bores 40 and 42 to communicate via these bores with suitably provided holes in the proximal end 33 of member 31. Similarly, air tube 36, rather than terminating at the proximal end 33 of member 31, may extend into or beyond the ear mold through bore 38.

A depth indicator 43 for indicating the extension of end 32 relative to the proximal end of probe assembly 30 takes the form of a flexible wire or string which is secured to the distal end area of air tube 36 or the narrow end of conical recess 35 and extends through that tube out through bore 38 in ear mold 34. Depth indicator 43 is color-coded or otherwise indexed so that as the balloon-like member 31 expands in a patient's ear, movement of the indices on indicator 43 into bore 38 render the expansion noticeable outside the ear. A particular index mark, when located at the entrance to bore 38, signifies full expansion of member 31.

When probe 30 is not in use it may be stored compactly with member 31, with tube 36 collapsed into the concave forward end of the ear mold 34. To this end, indicator 43 serves as a pull mechanism or drawstring to positively effect collapse when pulled through bore 38. Alternatively, if air tube 36 is made semi-rigid so as not to be fully collapsible, the air tube may serve as a guide support for insertion of the uninflated member 31 into the ear canal.

Assuming air tube 36 to be fully collapsible, probe 30 is deployed by fitting the ear mold or stop 34 into or against the patient's ear with the collapsed member 31 directed inward. The inlet and outlet tubes 39 and 41, respectively, are then connected to a suitable means for supplying pressurized test fluid, such as, for example, closed circulation pump such as that disclosed in U.S. Patent Application Ser. No. 762,437, by George Foti, filed Jan. 24, 1977, and entitled "PUMP FOR CLOSED CIRCULATION SYSTEM". Such supply means is schematically illustrated at P in FIG. 10. When the pump is energized, water or other test fluid under pressure is circulated through the balloon-like member 31 through test fluid inflow and outflow conduits 39 and 41. The balloon expands accordingly to conform to the contours of the patient's auditory canal (B2). If a hermetic seal is provided by ear mold 34, which is preferred the gradual expansion of member 31 requires the presence of air tube 36 and recess 35 to prevent air which is trapped in the ear from being pressurized and injuring the patient. Specifically, the expanding member 31 forces trapped air out through the air tube 36 and bore 38. An indication of the expansion of member 31 is provided by the continued withdrawal of indicator 43 into bore 38. When member 31 is fully expanded the conical recess 35 prevents the end of the air tube 36, which may be more rigid than the member 31, from being forced into painful contact with the patient's ear drum. Test fluid may begin to flow out through outflow tube 41 upon full expansion of member 31, and circulation of test fluid in member 31 then continued to more positively cause expansion of member 31. The thin material of member 31 effects efficient thermal transfer between the test fluid and the auditory canal.

It is important to note that the ear mold can be made in one size to provide a uniform fit in the tragus of most adults. This permits a standardization of testing procedures since the depth of penetration into the ear by member 31 is likewise uniform due to the stop function served by the proximal end of the ear mold.

The primary differences between probe 10 of FIG. 1 and probe 30 of FIG. 4 reside in the use of ear mold 34, the fact that the distal end 32 of probe 30 is not contoured to the tympanic membrane, and the absence of vanes 24 and 25. The transfer of thermal energy from probe 30 to areas of the auditory canal other than directly to the tympanic membrane is sufficient to induce nystagmus response without contouring the distal end to the tympanic membrane, although some touching of the tympanic membrane is preferable. The circulation within member 31, as forced by flow into inlet 39 and out of outlet 41, is sufficient without the need for vanes 24 and 25.

Typical dimensions for probe 30, for use with adult patients, are as follows: (a) the length A' from the proximal end 50 of ear mold 34 to the distal end 32 of member 31 (expanded) is 24.5 mm; (b) the diameter B' of member 31 expanded is 6 to 6.5 mm; (c) air tube 36 has an inner diameter of 0.25 mm and an outer diameter of 0.47 mm; (d) indicator 43 is attached approximately 1 to 3 mm from the tip of end 32 and has an outer diameter of 0.1 mm; (e) the length of ear mold 34 is 14 mm and the diameter C' at the proximal end 50 of the ear mold is 15 mm; and (f) the depth of the concavity in ear mold 34 is 4 mm. The thickness of the material comprising member 31 is on the order of 0.025 to 0.125 mm. The distal end of the air tube 36 begins approximately 2.5 mm from forward end 32 of member 31; that is, the axial length of recess 35 is approximately 2.5 mm. Indicator 43 is secured proximate this transition between the recess 35 and tube 36. It is to be understood that these dimensions are only examples of a specific embodiment and are not intended to limit the scope of the invention. Of course, all measurements must be scaled accordingly for use with adolescents, children and infants.

Although the technique described above for inserting the probe into a patient's ear assumes that member 31 is initially collapsed and then inflated after insertion, it should be noted that insertion may be effected when member 31 is partially or fully inflated. Under such circumstances air tube 36 still serves the function of permitting trapped air to egress from the ear canal as the canal is sealed by the expanded member 31 and ear mold 34. The inner surface of the patient's ear canal may be coated with an appropriate lubricant to facilitate sliding the probe along the ear canal during either insertion technique.

A modification 30' of probe 30 is shown in FIGS. 6 and 7 wherein all parts are designated with the reference numerals associated with corresponding parts in FIGS. 4 and 5. The modification in probe 30' comprises three additional conical recesses 44, 45 and 46 formed in distal end 32 of member 31. These recesses are equally spaced 120° apart about recess 35 as a center. Air tubes 47, 48 and 49 communicate with and extend from recesses 44, 45 and 46, respectively, to a common intersection point in air tube 36, which intersection point is typically spaced a distance K from the tip of end 32 of approximately 3 to 6 mm. The total of four ports in probe 30' further facilitates the egress of trapped air from the ear canal during insertion.

Still another embodiment of the invention is illustrated as probe 50 in FIGS. 8 and 9. Probe 50 differs from probe 30 only in that the air tube 36 and the cylindrical portion of member 31 between ends 32 and 33 is accordion-pleated or corrugated. The corrugation facilitates storage of member 31, when collapsed, into the concave region of ear mold 34; in addition, the corrugation strengthens member 31 against rupture when it is inflated. In the state illustrated in FIG. 8 member 31 is only partially expanded. When fully expanded the corrugations are completely flattened and member 31 assumes the configuration of probe 30 illustrated in FIG. 4. The corrugations in air tube 36 preferably remain folded slightly (although in stretched form) in the full expansion state of member 31 to provide additional strength against pressure build-up inside member 31.

A further embodiment 60 of the present invention is illustrated in FIG. 10. In this embodiment the only difference from probe of FIG. 4 is that air tube 36 is corrugated for the reasons discussed above. It should be noted that the four-inlet embodiment of FIG. 6 may be readily combined with the accordion-pleat feature of FIGS. 8 and 10.

The probe as described herein provides a simple, efficient and mess-free technique for applying caloric stimulus to the ear to produce nystagmus. The probe may be made to be disposable or re-usable, and is readily usable with existing test fluid supplies and nystagmus measurement apparatus. Although described as being generally cylindrical and having other specific configurations, it is to be understood that the shape of the probe is limited only in that it must fit in a patient's ear in a manner so that thermal transfer is efficiently achieved.

Likewise, it should be understood that a primarily important aspect of the probe is its ability to permit efficient thermal transfer between the ear canal and drum and the test fluid. In this regard, in probe 10 the material at end 12 (which end abuts the tympanic membrane) may differ from the material of the rest of the probe. For example, a thin sheet of thermally-conductive metal or a plastic impregnated with such metal may be used at end 12. I prefer, however, that the entire body be made of the same thin material since efficient thermal transfer characteristics are present in many types of polyurethanes and silicone elastomers when in suitably thin sheet form. Moreover, using a single material facilitates fabrication which may be by inexpensive injection molding techniques.

It should also be noted that a two-piece hinged ear mold may be used in conjunction with probe 10 of FIG. 1 or in place of ear mold 34. Such an ear mold would be contoured to fit the external anatomy and would be provided with bores necessary to permit the inlet and outlet tubes (and air tube) to pass through the mold.

The probes of the present invention may be used in numerous instances. For example:

(a) Evaluation of brain stem integrity of a comatose patient;

(b) Nystagmus inducing in comatose patient having basal skull fracture and concomitant cerebro-spinal otorrhea where open irrigation is not feasible because of possible meningeal contamination;

(c) Initial screening of vertiginous patient by internists and neurologists, particularly when performed in conjunction with the Foti pump described in the aforementioned patent application by George Foti;

(d) Sophisticated electro-nystagmus analysis;

(e) Nystagmus inducing whenever a perforation of the tympanic membrane is suspected, thereby precluding open irrigation of the ear canal.

An important advantage of the probe of the present invention resides in the fact that it conserves water and energy in comparison to prior caloric test procedures. Specifically, rather than having to heat large volumes of water, all of which is spilled over during conventional open flow caloric tests, the present probe uses a small volume of liquid which is continuously recycled through the probe. That liquid, once heated, requires only slight re-heating as it recirculates.

While I have described and illustrated one specific embodiment of my invention, it will be clear that variations of the details of construction which are specifically illustrated and described may be resorted to without departing from the true spirit and scope of the invention as defined in the appended claims. It would be, moreover, readily apparent to one skilled in the art that the structure embodying the invention could be used to carry out medical procedures in a body cavity other than the ear canal.

I claim:

1. The method of caloric vestibular testing comprising:

(a) inserting a flexible, thin-walled, distensible receptacle into an ear canal, the receptacle having provision for enabling circulation of pressurized calorized fluid therethrough and being inflatable by such fluid;

(b) admitting pressurized calorized fluid into the receptacle to cause its expansion laterally within the ear canal and longitudinally up to the tympanic membrane, such expansion filling the cross sectional area of at least a portion of the ear canal;

(c) while inflating the receptacle, venting air trapped between the receptacle and the tympanic membrane to atmosphere; and (d) circulating a volume of calorized fluid through the receptacle for a time period and at a temperature consistent with and while carrying out a caloric vestibular function testing procedure.

2. The method according to claim 1, including visually monitoring the degree of longitudinal expansion of the receptacle while it is being inflated by means of indicia located externally of the ear canal and moveable in direct relationship with longitudinal distension of the receptacle.

3. The method according to claim 1, wherein venting of air is carried out through a flowpath provided by the structural configuration of the receptacle and its associated structure.

4. The method according to claim 1, wherein venting of air is carried out through a conduit extending longitudinally through the receptacle and isolated from the interior of said receptacle.

* * * * *